United States Patent [19]

Cesaro

[11] 4,186,741

[45] Feb. 5, 1980

[54] AUTOMATIC INJECTING GUN FOR REMOTE CONTROLLED VACCINATION OF CATTLE, PIGS, AND ANIMALS IN GENERAL

[76] Inventor: Giulio Cesaro, Via Vittorio Veneto, 17, Vigodarzere (Province of Padova), Italy

[21] Appl. No.: 857,109

[22] Filed: Dec. 2, 1977

[30] Foreign Application Priority Data

Dec. 13, 1976 [IT] Italy .............................. 41700 A/76

[51] Int. Cl.² ................................................ A61M 5/00

[52] U.S. Cl. ............................ 128/218 P; 128/218 N

[58] Field of Search .................. 128/218, 173 H, 215, 128/220

[56] References Cited

U.S. PATENT DOCUMENTS

| | | | |
|---|---|---|---|
| 2,573,954 | 11/1951 | Casson | 128/173 H |
| 2,653,602 | 9/1953 | Smoot | 128/173 H |
| 3,353,537 | 11/1967 | Knox et al. | 128/218 R |
| 3,461,867 | 8/1969 | Zimmet et al. | 128/173 H |
| 3,504,673 | 4/1970 | Parisi | 128/218 R |
| 3,729,003 | 4/1973 | Hurschman | 128/218 DA |
| 3,790,048 | 2/1974 | Luciano et al. | 128/218 R |
| 3,976,069 | 8/1976 | Ong | 128/218 D |
| 4,007,739 | 2/1977 | Bron | 128/218 R |
| 4,103,684 | 8/1978 | Ismach | 128/173 H |

FOREIGN PATENT DOCUMENTS

| | | | |
|---|---|---|---|
| 969302 | 5/1958 | Fed. Rep. of Germany | 128/173 H |

*Primary Examiner*—Robert E. Bagwill

*Attorney, Agent, or Firm*—Guido Modiano; Albert Josif

[57] ABSTRACT

An automatic injecting gun for remote vaccination of cattle, pigs and animals in general comprises a gun body provided with a handle, an adjustable injector in the gun body for drawing vaccination liquid from a multi-dose container and discharging the vaccination liquid under control, a tubular duct engaging the injector and projecting from the gun body and an injection needle removably inserted on the end of the tubular duct not engaged with the injector.

4 Claims, 6 Drawing Figures

AUTOMATIC INJECTING GUN FOR REMOTE CONTROLLED VACCINATION OF CATTLE, PIGS, AND ANIMALS IN GENERAL

BACKGROUND OF THE INVENTION

This invention relates to an automatic injecting gun for remote controlled vaccination of cattle, pigs, and animals in general.

As is known, both animals bred on free grazing and in stable booths are subjected to periodic vaccination to prevent the insurgence of diseases.

This operation is often quite difficult to carry out, because animals tend to react in a threatening manner both to the presence of a foreign person (veterinarian) and to the introduction of a needle in their bodies.

Thus, it becomes necessary to keep the operator at a distance from the animal such as to remain out of its range.

Prior art techniques solve this problem by providing syringe extensions which, however, are not entirely successful either on accunt of their being awckward to handle or not ensuring a safe distance from the animal patient.

SUMMARY OF THE INVENTION

It is the technical task whereon this invention is based to provide an injecting gun that is practical and easy to operate, that operates automatically, and that is so designed as to afford at all times a safe distance of the operator from the animal.

Accordingly, it is an object of this invention to provide such a device which may be quickly and easily reloaded, such as to allow for a rapid sequence of operations as required when the animals are in a free state.

It is a further object of the invention to provide such a device, which is adjustable and wherein the amount of liquid to be injected can be easily predetermined according to the type of product being used and to the size of the animals to be vaccinated.

A not unimportant object of this invention is to provide an injecting gun which of simple construction as regards its basic components, and thus easy to clean and maintain.

The aforesaid task and objects are achieved, according to this invention, by an automatic injecting gun for remote controlled vaccination of cattle, pigs, and animals in general, characterized in that it comprises a gun body having a handle member an adjustable injector accommodated in said gun body and adapted to draw liquid from a multidose container and to discharge said liquid under control, a tubular duct including plural adjoinable sections and having an end engaging said injector and another end projecting from said gun body, and an injection needle removably inserted on said other end of said tubular duct not engaged with said injector, and a lever means adapted to load said injector against an elastic means effective to instantaneously discharge said injector under control by an operator.

BRIEF DESCRIPTION OF THE DRAWINGS

Further features and advantages of the invention will be apparent from the following description of a preferred embodiment thereof, illustrated in the accompanying drawings, where.

DESCRIPTION OF THE PREFERRED EMBODIMENTS

Figures 1, 2:
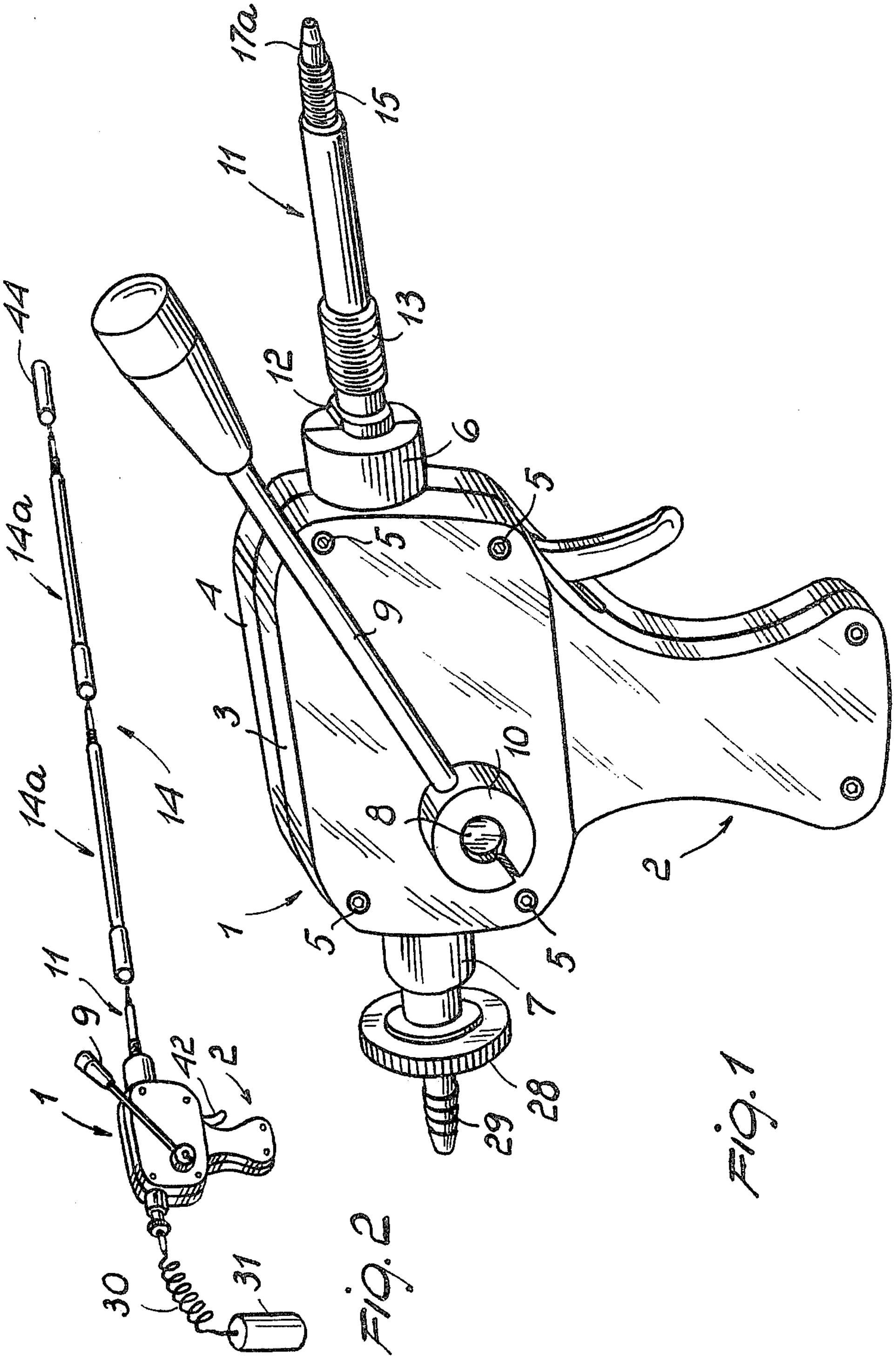
FIG. 1 is a perspective general view of the gun body according to the invention.
FIG. 2 is a perspective view of the component parts of the inventive gun.

With reference to the cited figures of the drawings, the gun body shown generally in FIG. 1 comprises an upper box-like portion 1 which is associated with a handle 2. In this embodiment the gun body is made up of two substantially similar shells 3 and 4, which are cast in a light and strong metal alloy such as magnesium aluminum, surface treated with an anodizing process.

Such two shells 3 and 4 are held together by a plurality of fastening capscrews 5 penetrating them and being arranged along the periphery of said gun body.

At their fronts, the two shells 3 and 4 have each a hemicylindrical lug which, upon matching the two shells together, produce a hollow cylindrical front fitting, inside threaded, indicated at 6.

Similarly, a hollow cylindrical rear fitting 7 projects rearwardly, which is also internally threaded and arranged to lay along the same axis as the front fitting 6.

These two fittings, 6 and 7, are useful for connecting other components of the invention, as will be explained hereinafter.

From the outer side of the shell 3, and more specifically from the right-hand side thereof as viewed by an operator holding the gun, of said box-like portion 1 there extends outwardly a shaft 8 which, as discussed hereinafter, is linked to internal mechanical parts and whereto is secured a loading lever 9 by means of a clamp hub 10.

Said lever 9 is located and movable in a plane perpendicular to said shaft 8.

Figures 4, 5, 6:
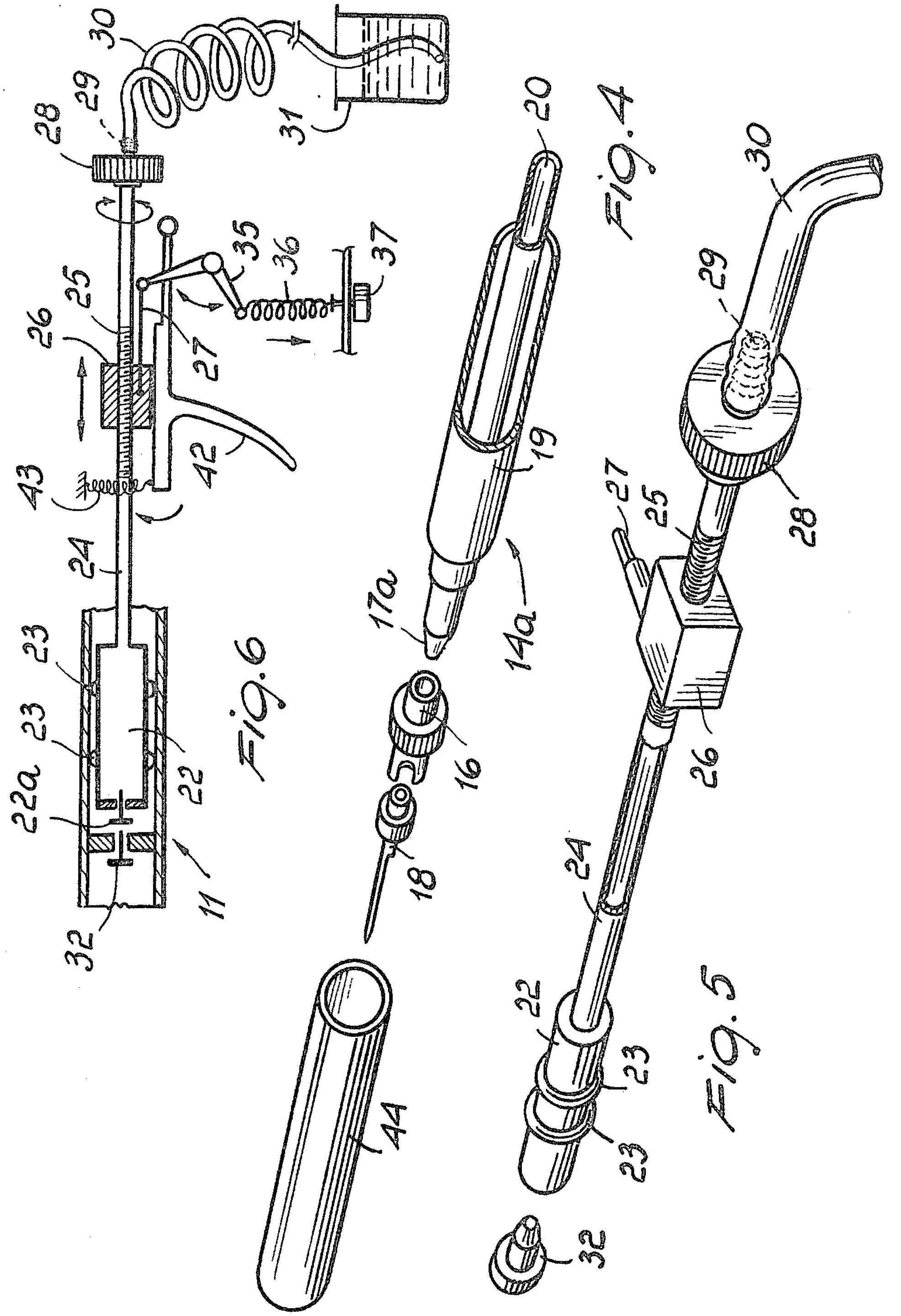
FIG. 4 is a partly sectional exploded perspective view of the termination of the tubular duct for the needle and needle guard.
FIG. 5 shows in perspective, partly in section, the plunger portion of the injector.
FIG. 6 is a diagram illustrating the operation of some components of the inventive injecting gun.

Into the threaded bore of said front fitting 6 an injector assembly is screwed comprising a hollow cylindrical body or member 11, which is provided externally, at its end next to the gun body, with a flange 12 with segments thereof removed to accomodate a tightening wrench; successively from said flange 12, said cylinder member or body has a first threaded area 13 of a larger diameter than the outer diameter of the cylindrical body 11—which is intended to threadably engage auxiliary elongation members such as a tubular duct indicated at 14 in FIG. 2—a second threaded area 15 having an outer diameter smaller than said cylindrical body 11, whereto a needle clamping sleeve, indicated at 16 in FIG. 4, will be threadably engaged, and finally a frustum-like lug 17 which is internally bored and serves as a matching seat for an injection needle, indicated at 18 in FIG. 4. Screw threads 13 and 15 constitute connector means for the needle means and the auxiliary elongation members.

As visible from the drawing the cylindrical member or body 11 has a cylinder cavity with an open and facing the inside of the box-like gun body 1.

The tubular duct 14, as shown in FIG. 2, comprises plural adjoinable sections **14*a*, each such sections being defined by a barrel 19 (FIG. 4) having an internally threaded end for threadably engaging said first threaded area 13, while the other end exactly mates the shape and threads of the cylindrical body 11, thereby it becomes possible to assemble any number of sections 14***a* together (FIG. 2) to obtain a predetermined operative distance for safe use.

The barrels 19, which also act as mechanical support members, accomodate a small tube 20 of a non-rigid plastic material serving as the delivery duct for the vaccinating liquid. At the front said small tube ends in a second frustum-like lug 17*a* (corresponding to the first frustum-like lug 17 of the cylindrical body 11), and at the other end in a hollow body, not shown, matching the lug 17.

Therefore, when an adjoinable section 14*a* is fully screwed in, a mechanical support through the barrel 19 and hydraulic continuity through the small tube 20 are provided up to the source of vaccination liquid 31 as will be described later.

When the gun is not in use, provision is made for a cap 44, which screws on similar to an extension barrel and acts as a needle guard or protection.

The hollow cylinder 11 contains a bored plunger 22 provided with two sealing O-rings 23 and having a head portion and a plunger cavity.

The plunger 22 extends in a hollow stem 24 which runs along the entire length of the box-like body 1 and exits said cylindrical fitting 7.

The hollow stem 24 includes an intermediate threaded area 25, whereon is inserted a metal block 26, the latter being provided with a position reference pointer 27 and, at its area extending out of the cylindrical fitting 7, with an adjusting nut 28, the rotation of which controls the positioning of the block 26.

The hollow stem 24 ends in a hose fitting 29 whereon a hose 30 is inserted which draws from a reservoir 31 containing the vaccine to be injected.

Within the plunger 22, in the head portion thereof there is provided a check valve 22*a* which opens as the plunger is withdrawn to allow liquid into the cylindrical body 11. A first check valve 32 is located at the top of said cylindrical body in the cylinder cavity thereof and opens as the plunger is moved forward, i.e. during the injection step.

Between the first and the second check valves 32 and 22*a* a cylinder chamber is delimited in the cylinder cavity of the cylinder member 11.

Figure 3:
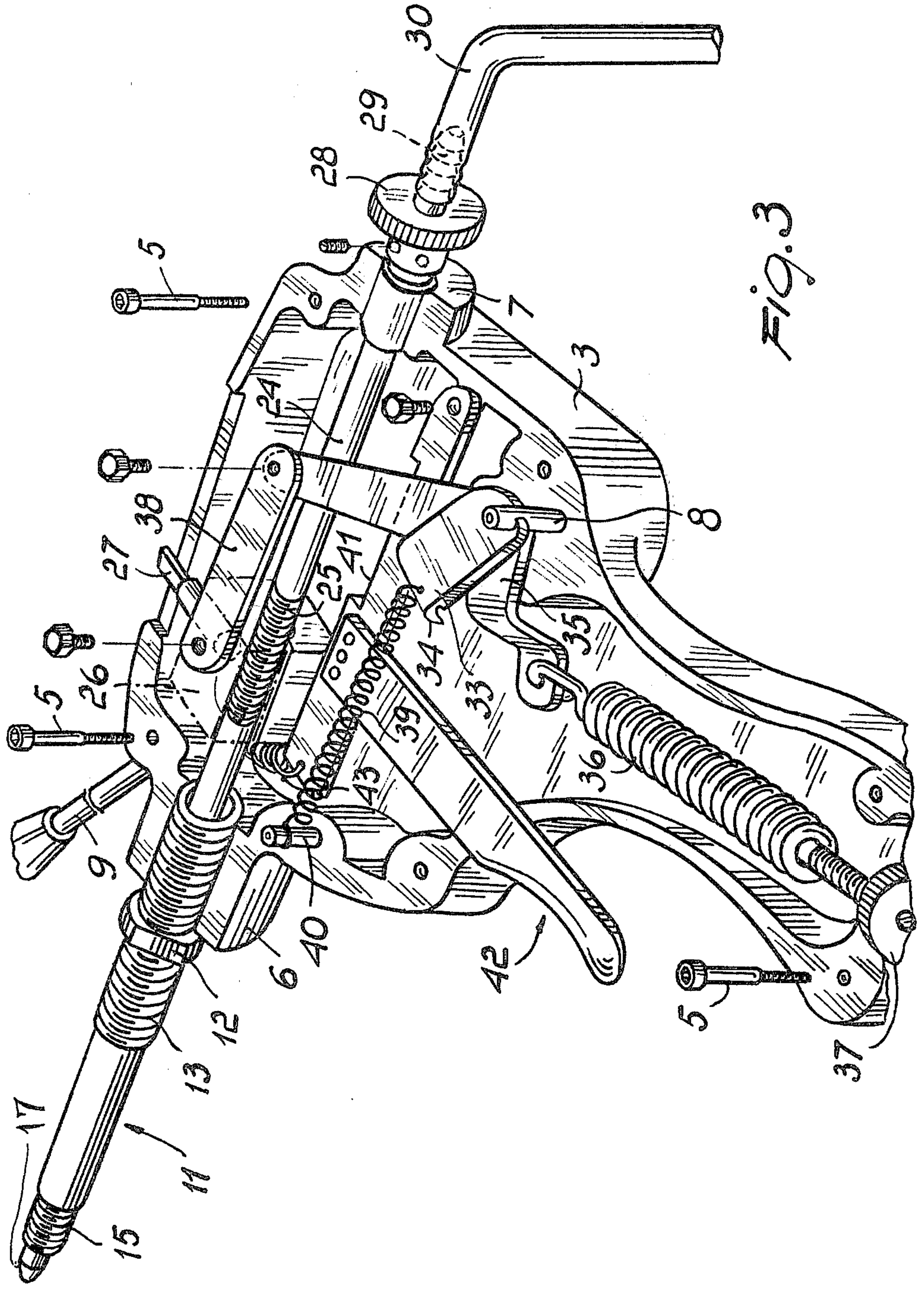
FIG. 3 is a partly exploded perspective view of the mechanism contained in the gun body.

The plunger movements are achieved by rechargeable springed release means in the form of articulated spring loaded lever means, illustrated in FIG. 3: as described, said lever 9 is locked onto a shaft 8 which is rigid, on the inside, with a plate 33 formed with a bent projection 34 which interferes, in its movement, with an "L" shaped lever 35, which at one end is connected to a load spring 36 that is adjustable by means of an adjusting screw 37 projecting out of the grip 2, and at the other end is connected to the block 26 through a return plate 38. Said plate 33 is biassed to return to a rest or inoperative position by a tension spring 39 acting between that plate and an anchor pin 40 formed on the shell 3.

Provision is also made for an actuating trigger means 42 formed comprising a trigger lever 42' and a trigger bar 42" with a notch 41 adapted to engage the block 26 owing to the trigger bar 42" being biassed by a spring 43.

The injecting gun according to this invention operates in the following manner.

Before using it, the gun is adjusted such that the amount of liquid injected is proportioned to the type of product being used and the size of the animals to be vaccinated. This is obtained by turning the adjusting nut 28, and accordingly the hollow stem 24 which, by virtue of its intermediate threaded area 25, displaces the block 26 to a position closer to or farther from the notch 41 of the trigger 42. Thus, the plunger stroke length is reduced or increased since, while the forward travel limit of the plunger 22 remains fixed as defined by the head of the cylindrical body 11, its rearward travel limit is displaced depending on the distance of the block 26 from the notch 41.

From the foregoing it will be understood that the block 26 and the notch 41 operate as adjustable limit stop means for the plunger 22 and the trigger bar 42" and its notch 41 define stop surface means.

Once the stroke of the plunger 22 has been adjusted, and thus the amount of liquid that can be injected, as visually indicated by the position reference pointer 27, the load spring 36 may be adjusted, if required, through the adjusting screw 37, such as to vary the force and ejection velocity of the liquid as a function of the viscosity, amount and type of the liquid.

The injecting gun is then loaded by operating the loading lever 9; the plate 33, being rigid with the shaft 8 of the lever 9, rotates and interferes through its bent projection 34 with the "L" shaped lever 35, which is in turn rotated to put under tension the load spring 36 and concurrently withdraw the block 26, hollow stem 24 and plunger 22. Thus, a suction effect is created within the cylindrical body 11 which causes the second check valve 32 to close and the check valve 22*a* to open, therefore permitting the liquid to flow from the reservoir 31, through the hose 30, hollow stem 24, and plunger 22. In its rearward movement, the block 26 inserts itself in the notch 41 owing to the trigger 42 being recalled by the spring 43. In this position, the device is loaded and ready for use. By depressing the trigger 42, the block 26 is disengaged from the notch 41, thereby the spring 36 causes the plunger 22 to move at high velocity and, owing to the pressure thus created, close the check valve 22*a*, open the check valve 32, and eject the liquid through the small tubes 20 and needle 18.

The invention fully achieves it objects. Noteworthy are, in fact, its convenience of operation and the absolute safety enjoyed by the operator who by adding or removing barrel sections is enabled to select the optimum operative distance. Furthermore, this injecting gun is easy to handle, quick in operation and adjustable with high accuracy.

As regards it construction materials, magnesium aluminum alloy is preferred for the barrels, and possibly for the gun body as well, while stainless steel is preferred for the plunger, passages and valves, such as lightweight and a good balance may be ensured, thanks to the low density of magnesium-aluminum alloy.

However, these materials, as well as others mentioned in the foregoing description, should not be construed in a restrictive sense. Moreover, all of the details may be substituted with other technically equivalent elements.

I claim:

1. An injecting gun for controlled vaccination of cattle, pigs and animals in general, comprising a supporting box-like gun body having an extension in the form of a handle, an injector assembly supported by said box-like gun body, said injector assembly having a hollow elongated cylinder member with a cylinder cavity having an open ended portion thereof fixed on said box-like body and facing the interior thereof and an opposite end portion thereof projecting outside said box-like body, said opposite end portion having connector means for selectively connecting thereto needle means and auxiliary elongation members, a hollow plunger member with a head portion and a plunger cavity and slidable within said cylinder cavity, a first check valve structure within said cylinder cavity arranged in a position more remote from said open end of the cylinder member than said plunger head portion to define therebetween a cylinder chamber the length whereof being defined by the actual position of said plunger member, a second check valve structure in the head portion of said plunger member, said first check valve structure controlling the flow of vaccination liquid from said chamber towards said opposite end portion of the cylinder cavity and vice versa to prevent such flow when the liquid pressure in said opposite end portion cavity is higher than the liquid pressure in said cylinder chamber and to allow such flow when the pressure conditions are reversed, said second check valve structure controlling the flow of vaccination liquid from said cylinder chamber towards said plunger caivty and vice versa to prevent liquid passage from said cylinder chamber towards said plunger cavity when the liquid pressure within said cylinder chamber is higher than the liquid pressure within said plunger cavity and to allow such passage when the pressure conditions are reversed, duct means for connecting the plunger cavity with a source of vaccination liquid, adjustable limit stop means for said plunger to adjust the maximum volume of said cylinder chamber and trigger means and rechargeable springed release means for said plunger member to actuate the injection action of said plunger member, when said trigger means are triggered.

2. Injecting gun according to claim 1, wherein said auxiliary elongation members comprise at least one elongated barrel member having connection means at both end portions thereof cooperating at one end thereof with said connector means and at the other end thereof with said needle means and duct means for hydraulic communication thereof with said cylinder cavity.

3. Injecting gun according to claim 1, wherein said plunger comprises an elongated hollow stem rotatable about its axis and in hydraulic communication with the plunger cavity and with said duct means, and wherein said adjustable limit stop means comprise an outer screw thread on said elongated stem, a block member in screwing engagement with said outer screw thread thereby to shift said block member along said elongated stem when said stem is rotated and said block member is prevented from rotation and a stop surface member included in said trigger means in the path of said adjustable block member normally to hold said block member in the position in which said rechargeable springed release means are charged and to release said block member when said trigger means are triggered.

4. An injecting gun for controlled vaccination of cattle, pigs and animals in general, comprising a supporting box-like gun body having an extension in the form of a handle, an injector assembly supported by said box-like gun body, said injector assembly having a hollow elongated cylinder member with a cylinder cavity having an open ended portion thereof fixed on said box-like body and facing the interior thereof and an opposite end portion thereof projecting outside said box-like body, said opposite end portion having connector means for selectively connecting thereto needle means and auxiliary elongation members, a hollow plunger member with a head portion and a plunger cavity and rotatable and slidable within said cylinder cavity, a first check valve structure within said cylinder cavity arranged in a position more remote from said open end of the cylinder member than said plunger head portion to define therebetween a cylinder chamber the length whereof being defined by the actual position of said plunger member, a second check valve structure in the head portion of said plunger member, said first check valve structure controlling the flow of vaccination liquid from said chamber towards said opposite end portion of the cylinder cavity and vice versa to prevent such flow when the liquid pressure in said opposite end portion cavity is higher than the liquid pressure in said cylinder chamber and to allow such flow when the pressure conditions are reversed, said second check valve structure controlling the flow of vaccination liquid from said cylinder chamber towards said plunger cavity and vice versa to prevent liquid passage from said cylinder chamber towards said plunger cavity when the liquid pressure within said cylinder chamber is higher than the liquid pressure within said plunger cavity and to allow such passage when the pressure conditions are reversed, duct means for connecting the plunger cavity with a source of vaccination liquid, said plunger having a hollow stem extending into the interior of said box-like body and supported thereby rotatable about its axis together with said plunger and in hydraulic communication with said plunger cavity and with said duct means, an outer screwthread on said elongated stem, a block member within said interior of said box-like body, said block member engaging with said outer screwthread of said hollow stem thereby to shift said block member along said stem when said stem is rotated and said block member is prevented from rotation, articulated spring loaded lever means conneted with said block member to shift said block member together with said stem and said plunger in the direction of the axis of said stem from a released position in which the plunger is in its fully extracted position nearest to said first check valve structure into a recharged position in which the plunger is in its fully withdrawn position remote from said first check valve when said spring loaded articulated lever means are hand actuated thereby to suck vaccination liquid from said source of vaccination liquid into said cylinder chamber, a trigger bar biased towards the path of said block member and having a notch in engagement with said block member when said block member has been shifted together with said stem into its re-charged position and a trigger lever connected with said trigger bar adapted when triggered to move said trigger bar away from said block member and release said block member to allow said spring loaded lever means to throw said block member together with said stem and said plunger into the fully extracted position thereof and thereby expel the vaccination liquid contained in said cylinder chamber therefrom and cause it to reach said needle means and be ejected therefrom.

* * * * *